United States Patent
Dobson et al.

(10) Patent No.: US 9,767,552 B2
(45) Date of Patent: Sep. 19, 2017

(54) SYSTEMS AND METHODS FOR DETECTING THE PRESENCE OF ANOMALOUS MATERIAL WITHIN TISSUE

(75) Inventors: Jon Paul Dobson, Gainesville, FL (US); Mark Rogers Davidson, Florahome, FL (US); Yunmei Chen, Gainesville, FL (US); Keith David White, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 343 days.

(21) Appl. No.: 14/342,976

(22) PCT Filed: Sep. 6, 2012

(86) PCT No.: PCT/US2012/053916
§ 371 (c)(1),
(2), (4) Date: Apr. 17, 2014

(87) PCT Pub. No.: WO2013/036607
PCT Pub. Date: Mar. 14, 2013

(65) Prior Publication Data
US 2014/0219535 A1 Aug. 7, 2014

Related U.S. Application Data (60) Provisional application No. 61/531,276, filed on Sep. 6, 2011.

(51) Int. Cl.
*G06T 7/00* (2017.01)
*G01R 33/50* (2006.01)
*G01R 33/56* (2006.01)
*A61B 5/00* (2006.01)

(52) U.S. Cl.
CPC ............ *G06T 7/0012* (2013.01); *G01R 33/50* (2013.01); *G01R 33/5608* (2013.01);
(Continued)

(58) Field of Classification Search
None
See application file for complete search history.

(56) References Cited

U.S. PATENT DOCUMENTS

2004/0102692 A1 * 5/2004 Schenck ................ A61B 5/055
600/410
2005/0020904 A1 1/2005 Cline et al.
(Continued)

FOREIGN PATENT DOCUMENTS

JP 2006507902 A 3/2006
WO 2010051267 A1 5/2010

OTHER PUBLICATIONS

Haacke, E. Mark, et al. "Imaging iron stores in the brain using magnetic resonance imaging." Magnetic resonance imaging 23.1 (2005): 1-25.*
(Continued)

*Primary Examiner* — Vikkram Bali
*Assistant Examiner* — Tracy Mangialaschi
(74) *Attorney, Agent, or Firm* — Thomas Horstemeyer, LLP (57) ABSTRACT

In one embodiment, the presence of anomalous material within tissue is detected by scanning a patient using magnetic resonance imaging (MRI) to obtain MRI data, identifying individual voxels of the MRI data, identifying multiple parameters of each voxel, and determining as to each voxel based upon the identified parameters the likelihood of tissue represented by the voxel containing anomalous material.

27 Claims, 5 Drawing Sheets

(52) U.S. Cl.
CPC ......... *A61B 5/4088* (2013.01); *G06T 2200/04* (2013.01); *G06T 2207/10088* (2013.01); *G06T 2207/20076* (2013.01); *G06T 2207/30016* (2013.01)

(56) References Cited

U.S. PATENT DOCUMENTS

| | | |
|---|---|---|
| 2005/0215883 A1 | 9/2005 | Hundley et al. |
| 2010/0127704 A1* | 5/2010 | Warntjes ............... G01R 33/56 324/309 |
| 2013/0034282 A1* | 2/2013 | Kaufman .............. G06T 7/0014 382/128 |

OTHER PUBLICATIONS

Hocq, Aline, et al. "Variable- field relaxometry of iron- containing human tissues: a preliminary study." Contrast media & molecular imaging 4.4 (2009): 157-164.*

Schenck, John F., et al. "High-field magnetic resonance imaging of brain iron in Alzheimer disease." Topics in Magnetic Resonance Imaging 17.1 (2006): 41-50.*

Clark, Paul R., and Timothy G. St Pierre. "Quantitative mapping of transverse relaxivity (1/T 2) in hepatic iron overload: a single spin-echo imaging methodology." Magnetic resonance imaging 18.4 (2000): 431-438.*

Foreign search results for PCT/US2012053916, dated Apr. 7, 2015.

Haacke, et al., Imaging iron stores in the brain using magnetic resonance imaging, vol. 23, No. 1, Jan. 1, 2005.

Zhiyue, et al., Evaluation of iron overload by single voxel MRS measurement of liver T2; Journal of Magnetic Resonance Imaging, vol. 15, No. 4, Apr. 27, 2002.

Aline, et al., Variable-field relaxometry of iron-containing human tissues; a preliminary study; Contrast Media & Molecular Imaging, vol. 4., No. 4, Jul. 1, 2009.

Chen, et al., An integrated neighborhood correlation and hierarchical clustering approach of functional MRI, IEEE transactions on Biomedical Engineering, vol. 53, No. 3, Mar. 1, 2006.

Japanese Office Action of Jul. 5, 2016 for 2014-529843.

* cited by examiner

SYSTEMS AND METHODS FOR DETECTING THE PRESENCE OF ANOMALOUS MATERIAL WITHIN TISSUE

CROSS-REFERENCE TO RELATED APPLICATION

This appliction is the 35 U.S.C. §371 national stage of PCT Application No. PCT/US2012/053196, entitled "Systems and Methods for Detecting the Presence of Anomalous Material within Tissue" and filed Sep. 6, 2012, which is herein incorporated by reference in its entirety and which also claims priority to, and the benefit of, U.S. Provisional Application No. 61/531,276, filed Sep. 6, 2011, which is herein incorporated by reference in its entirety.

STATEMENT REGARDING FEDERALLY SPONSORED RESEARCH OR DEVELOPMENT

This invention was made with Government support under contracts 5 R21 NS060304 awarded by the National Institutes of Health. The Government has certain rights in this invention.

BACKGROUND

Alzheimer's disease currently affects over 35 million people worldwide and the effects of the disease are devastating to patients as well as their families and caretakers. It is estimated that the global cost of Alzheimer's disease is $315 billion annually. While a great deal of progress has been made in understanding the biochemical basis for the disease and in developing compounds to slow its progression, this knowledge has yet to be translated into a treatment, cure, or even a reliable diagnostic technique.

One aspect of the neurochemistry that shows promise is the identification of iron as a biomarker for Alzheimer's disease. Over the past several years, researchers have worked on locating and characterizing unusual iron oxide particles that form in association with neurodegenerative diseases such as Alzheimer's disease, and it has been determined that magnetite and other iron oxides tend to form in brain tissue in association with such diseases. It is now believed by some that excess or unusual iron oxides, such as magnetite, may be formed early in the Alzheimer's disease process, possibly due to a malfunction of the normal iron storage protein, ferritin. If iron oxides associated with neurodegeneration could be detected early in the progression of the disease, new treatments could be developed and existing treatments could be initiated earlier. Early treatment is of particular importance in the case of Alzheimer's disease because much of the tissue in critical areas of the brain may already be irreparably damaged by the time symptoms appear.

Synchrotron radiation has been used to locate and characterize iron in post-mortem brain tissue. However, such radiation cannot be applied to living patients. Although several attempts have been made to identify iron using magnetic resonance imaging (MRI), such attempts have been largely unsuccessful. Many of these attempts have been focused on regional changes in MRI signals due to regional iron accumulation. Such attempts have for the most part not resulted in the detection of clinically relevant, statistically significant differences between signals from control and diseased tissue. One reason for this may be that regional changes are not sufficiently correlated with the disease process. In addition, the signals used to identify iron concentration may be confounded by other tissue effects that produce changes similar to those of iron, such as changes in tissue magnetic susceptibility or proton concentration. Furthermore, the averaging of MRI signals at a large spatial scale that is typically performed in MRI may obscure the signatures of iron concentrated on small spatial scales.

From the above discussion, it can be appreciated that it would be desirable to have an alternative system and method for detecting the presence of iron within tissue, such as brain tissue.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an alternative system and method for detecting the presence of iron within tissue, such as brain tissue. Disclosed herein are embodiments of systems and methods for detecting the presence of anomalous material, such as iron, in tissue, such as brain tissue. In one embodiment, the influence of iron and/or iron compounds associated with neurodegenerative disease within brain tissue is characterized and identified using a process in which individual voxels of magnetic resonance imaging (MRI) data are evaluated using multiple different modes of analysis. In one example method, T1, T2, and T2* MRI relaxometry scans are performed and the MRI voxels are individually analyzed to develop a score that is indicative of whether or not anomalous concentrations and/or forms of iron are present in the tissue represented by the voxel.

In the following disclosure, various embodiments are described. It is to be understood that those embodiments are example implementations of the disclosed inventions and that alternative embodiments are possible. All such embodiments are intended to fall within the scope of this disclosure.

Figure 1:
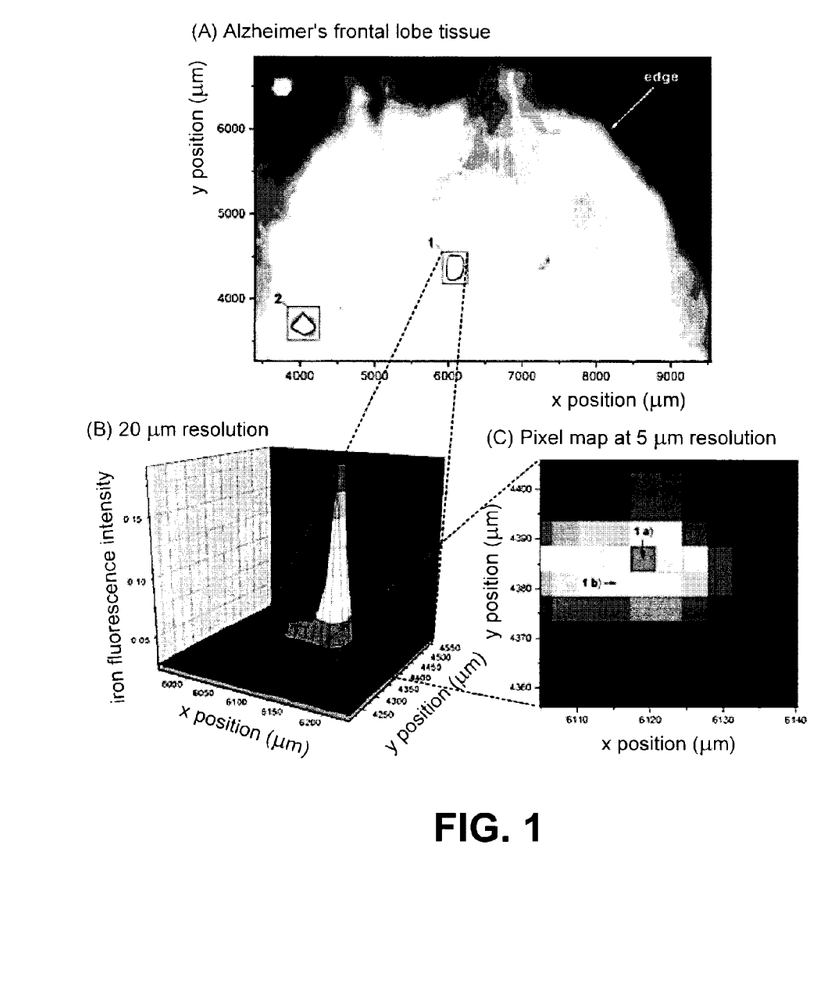
FIGS. 1A-1C are images of iron anomalies in Alzheimer's disease tissue shown in low-, medium-, and high-resolution, respectively.

Current clinical studies of brain iron as a potential biomarker for neurodegeneration rely on assumptions that signal changes in MRI are due to iron, where interpretation of data is often based on post-mortem measures of iron in tissues. However, this interpretation is complicated in patient analysis by the competing effects of brain iron accumulation and tissue degeneration, as well as the inhomogeneous and highly localized distribution of anomalous iron compounds within the diseased tissue. This is apparent from FIG. 1, which provides a map of iron anomalies in an Alzheimer's disease tissue section. FIG. 1A is an initial low-resolution (200 μm/pixel) contour map of the tissue section, FIG. 1B is a medium-resolution scan of area 1 in FIG. 1A, revealing that the source of the bright spot in FIG. 1A is located within a 20 μm pixel, and FIG. 1C is a high-resolution scan within FIG. 1B, locating the source of the high intensity spot at 5 μm/pixel.

Researchers have noted that changes in small scale homogeneity are more important in affecting T2 shortening than overall, bulk iron composition, further confounding simple interpretation of T2 data. Some groups have worked on resolving some of these confounding issues by comparing MRI analysis of mouse model brains containing plaques with post-mortem staining for iron and plaque. Others have used multiple field MRI to deconvolute the effect of iron on the T2 shortening from other effects such as viscosity changes and have indeed found regional changes in field dependent T2 shortening associated with Alzheimer's disease. However, these findings are not easily translated into a practical clinical method.

Alzheimer's disease plaques have been examined ex-vivo using transmission electron microscopy (TEM) tomography and magnetite nanoparticles have been found in the cores. In a recent study, MRI T2 images were successfully used in diagnosis of subtypes of NBIA by combining radiological judgments of intensity and location. While these and other studies suggest that T2 may be used for imaging plaques, the effect has yet to be translated into a method for reliable clinical diagnosis. This is likely due to the complexity of confounding factors in T2 shortening. In addition, since the magnetic iron particles associated with plaques are often widely dispersed, the effects may only be seen in single voxels in clinical MRI scans. These individual voxels may be dismissed as noise or averaged by the internal clinical image processing methods.

Disclosed herein are novel, multimodal, MRI-based detection techniques based upon the knowledge that has been gained on the chemical nature and widely dispersed distribution of magnetic iron compounds related to Alzheimer's disease. As is described below, the disclosed technique exploits both regional inhomogeneity in relaxation shortening as well as the highly localized nature of magnetic iron deposits in the brains of those affected. The disclosed methods are only partially based upon the amount of iron present in regional areas of the brain, and rather focus on the location, number, and distribution of anomalous magnetic iron-containing MRI voxels. By combining regional comparisons of T1, T2, and T2* relaxometry data with tests of localized changes to relaxation in individual voxels, much of the ambiguity faced by examining iron changes with single-modal analysis of MRI can be overcome and a reliable, effective, and non-invasive Alzheimer's disease diagnostic test can be achieved.

In the disclosed systems and methods, MRI data is collected and that data is analyzed, optimally prior to any image enhancement, to identify individual voxels that represent magnetic iron-containing tissue. In one embodiment, a figure-of-merit score is developed for each voxel based upon a combination of voxel parameters that are indicative of the likelihood of anomalous iron being present. By evaluating each voxel in this manner, and comparing it to its nearest neighbors as a measure of its anomalous nature across a population of voxels, a determination can then be made as to the likelihood of the patient having Alzheimer's disease or another neurodegenerative disease.

Figure 2:
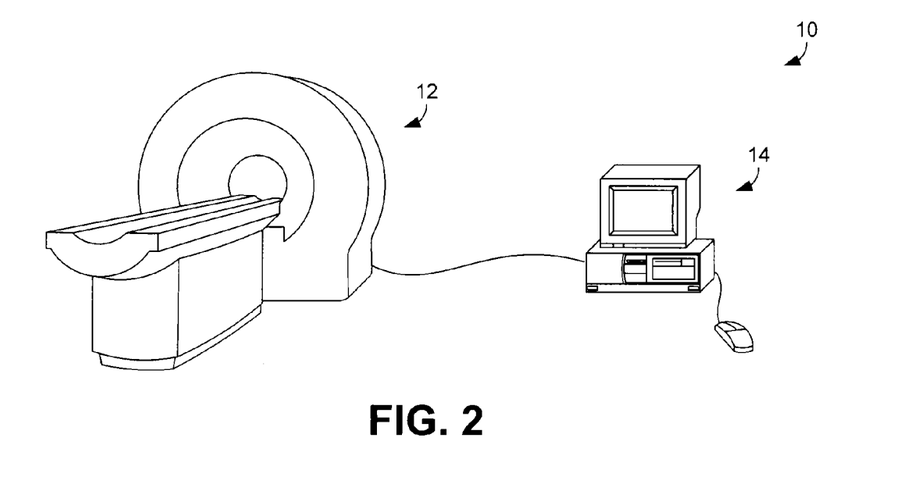
FIG. 2 is a schematic diagram of an embodiment of a system for detecting the presence of iron within tissue.

FIG. 2 illustrates an example system 10 for detecting the presence of anomalous material, such as iron, within tissue. As is shown in that figure, the system 10 generally includes an image capture device 12, in the form of an MRI machine, and a computing device 14 that is placed in communication with the image capture device. The computing device 14 obtains image data captured by the image capture device 12 and evaluates that data to identify the presence of iron within scanned tissue.

Figure 3:
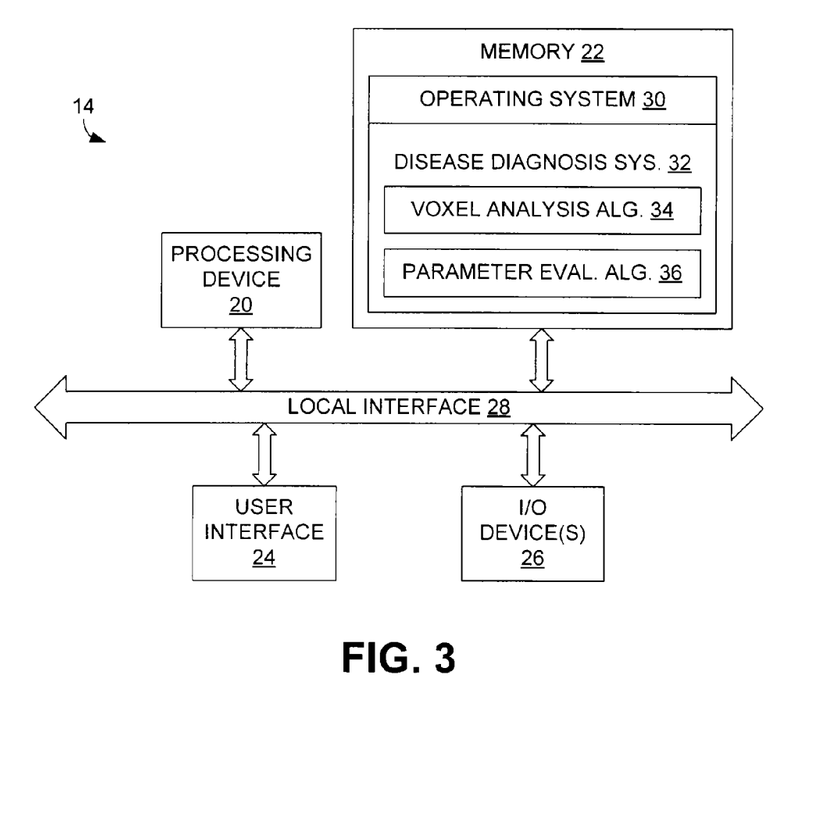
FIG. 3 is a block diagram of a computing device shown in FIG. 2.

FIG. 3 illustrates an example architecture for the computing device 14 shown in FIG. 2. As is indicated in FIG. 3, the computing device 14 generally comprises a processing device 20, memory 22, a user interface 24, and at least one I/O device 26, each of which is connected to a local interface 28.

The processing device 20 can comprise substantially any processor capable of executing instructions stored within the memory 22. The memory 22 can include any one or a combination of volatile memory elements (e.g., random access memory (RAM)) and nonvolatile memory elements (e.g., hard disk, compact disc (CD), flash memory, etc.). The user interface 24 comprises the components with which a user interacts with the computing device 14, and the I/O devices 26 are adapted to facilitate communications with other devices.

Stored within memory 22 are various programs and/or algorithms (logic), including an operating system 30 and a disease diagnosis system 32. The disease diagnosis system 32 is configured to analyze data captured with the image capture device 12 and to identify anomalous material, such as iron, within the tissue that was scanned. In some embodiments, the anomalous material is identified using one or more voxel analysis algorithms 34 of the disease diagnosis system 32. In addition, the disease diagnosis system 32 can include one or more parameter evaluation algorithms 34 that are used to determine weighting factors that are to be applied to the various parameters considered by the voxel analysis algorithm(s) 34. Examples of operation of the disease diagnosis system 32 and its algorithms are described below. Although the system 32 and algorithms 34, 36 are shown as being resident on the computing device 14, it is noted that they can be stored elsewhere and still be used in the same manner. Moreover, it is noted that the system 32 and/or algorithms 34, 36 can form an independent software package or can be integrated into an MRI software package.

Figure 4:
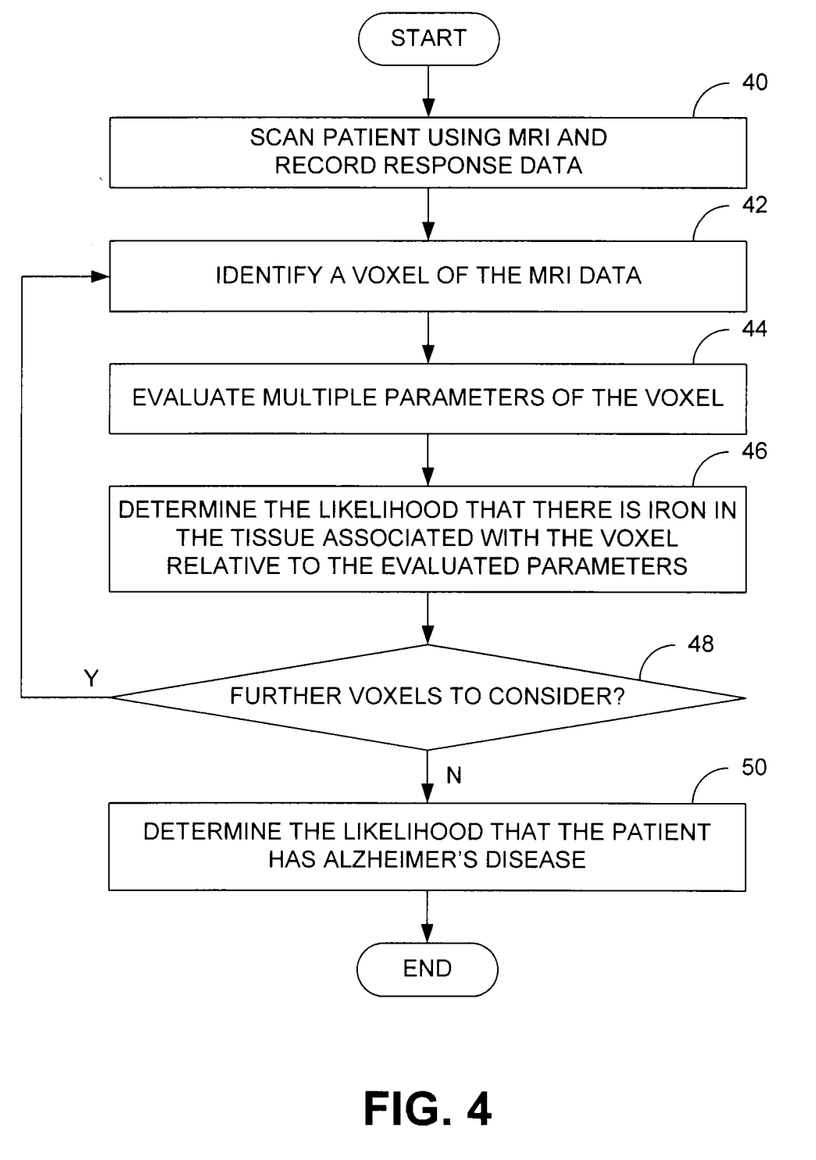
FIG. 4 is a flow diagram of a first embodiment of a method for detecting the presence of anomalous material within tissue.

FIG. 4 provides an overview of an embodiment of a method for detecting anomalous material within tissue and therefore determining the likelihood of a patient having a disease. Although the discussion of FIG. 4 is focused on detecting iron and diagnosing Alzheimer's disease, it is noted that the described method could be used to identify the presence of other neurodegenerative diseases of which the presence of iron is indicative, or traumatic brain injury that leads to intracranial bleeding and the potential formation of magnetic iron compounds derived from iron in the blood. Moreover, the described method, or one similar to it, could more generally be used to identify the presence of anomalous materials that may be associated with other disease processes, such as Parkinsons' disease, Huntington's disease, or diseases that additionally affect other organs with iron overload, such as hemochromatosis.

Beginning with block 40, a patient is scanned using an MRI machine and the relaxation data is recorded. The patient can be scanned using any one of a number of MRI modalities. For example, any one of a T1 relaxometry scan, a T2 relaxometry scan, or a T2* relaxometry scan can be performed. In some embodiments, the patient is scanned using multiple MRI modalities. For instance, each of a T1, T2, and T2* relaxometry scan can be performed. In still other embodiments, other types of MRI scans can be performed to provide additional or substitutional data for evaluating the patient tissue. When multiple scans are performed, they can be performed in quick succession to minimize misregistration of the MRI data. One or more registration algorithms can be used, if needed, to ensure alignment of the data.

Referring next to block 42, a voxel of the recorded MRI data is identified. At this point, multiple parameters of the identified voxel can then be evaluated, as indicated in block 44. In some embodiments, the voxel parameters are evaluated using the voxel analysis algorithm(s) 34 discussed in relation to FIG. 3. The evaluated parameters are those that may be indicative of the presence, or absence, of iron within the tissue represented by the voxel. Example parameters are described below in relation to FIG. 5.

Irrespective of the parameters that are evaluated, a determination can be made as to the likelihood that there is iron in the tissue represented by the voxel, as indicated in block 46. In some embodiments, each of the evaluated parameters is assigned a particular weight that relates to the strength of the parameter in predicting the presence of iron. In some embodiments, weighting factors or coefficients are determined using the parameter evaluation algorithm(s) 36 identified in FIG. 3 based upon clinical data collected from both healthy and diseased brain tissue. In some embodiments, the parameter evaluation algorithm(s) 36 applies a linear regression method to determine how closely correlated each parameter is to the presence of iron in the tissue. Once the weighting factors have been determined, they can be used in all subsequent diagnoses for the disease that is being diagnosed. Notably, different weighting factors may apply for different diseases because different parameters may be better predictors of the presence of anomalous materials for different diseases.

In some embodiments, the parameters are summed, after application of their individual weighting factors, to obtain a numerical figure-of-merit score that provides an indication of the likelihood that there is iron in the tissue represented by the voxel under consideration. For example, a relatively high score can indicate a high likelihood of anomalous iron being present, while a relatively low score can indicate a low likelihood of anomalous iron being present.

After the likelihood of the tissue represented by the voxel containing iron has been determined, flow can return to block 42 (via decision block 48) and the next voxel of the MRI data can be analyzed in the same manner as that described above. Flow continues in this manner until each voxel has been evaluated. In some embodiments, this will result in a score being assigned to each voxel. At this point, flow continues on to block 50 at which the likelihood of the patient having Alzheimer's disease can be determined. This determination can be made relative to the determined voxel scores. For example, a threshold score can be established above which the tissue is assumed to contain iron. The number of voxels having a score greater than the threshold can then be counted. If the total number of iron-containing voxels exceeds a further threshold, the disease diagnosis system 32 can provide an indication to a physician that the patient likely has Alzheimer's disease. Of course, all scoring data can be provided to the physician to enable him or her to make his or her own diagnosis.

It is noted that, because the volumes of relevant regions of interest will vary by disease, and because total brain volumes will vary between patients, a given patient may tolerate different numbers of anomalous voxels without acquiring the disease under consideration. For example, a medium-sized hippocampus in a small brain might tolerate a given load of anomalous voxels better than does the same load of anomalous voxels in the same volume of hippocampus within a large brain. In some embodiments, the disease diagnosis system 32 can be configured to account for such variations. For example, the system 32 can base the disease diagnosis upon a relative concentration of anomalous voxels instead of the total number of anomalous voxels. Notably, other factors can also be taken into account, such as age-related differences that may have a significant clinical impact.

Because there are physiological differences from patient to patient (e.g., how much water is present in the brain), it may be advisable to calibrate the system for each patient before performing the above-described method. In such a case, the level of iron effect for a given patient can be quantified relative to other patients or an established standard. In some embodiments, such calibration can be performed by providing an additional coil in the MRI machine and using the coil to apply a known magnetic field to the patient. A first T2* relaxometry scan can then be performed without the magnetic field applied, and a second T2* relaxometry scan can be performed with the magnetic field applied to observe the change in response and provide a known calibration point. Example apparatuses and methods for performing such calibration are described in U.S. Pat. No. 7,863,896, which is hereby incorporated by reference in its entirety into this disclosure.

Figure 5A:
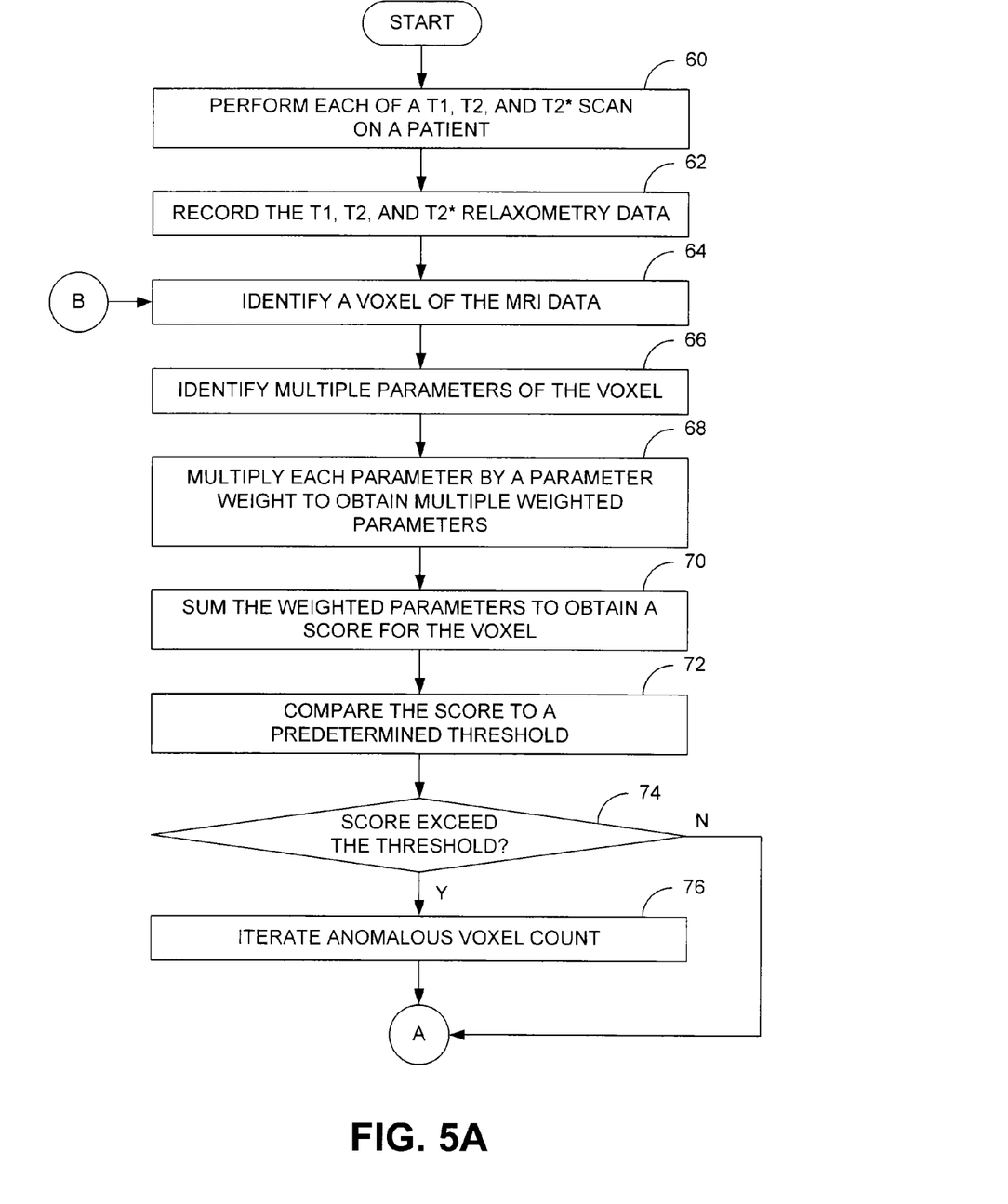
FIGS. 5A and 5B present a flow diagram of a second embodiment of a method for detecting the presence of anomalous material within tissue.
Figure 5B:
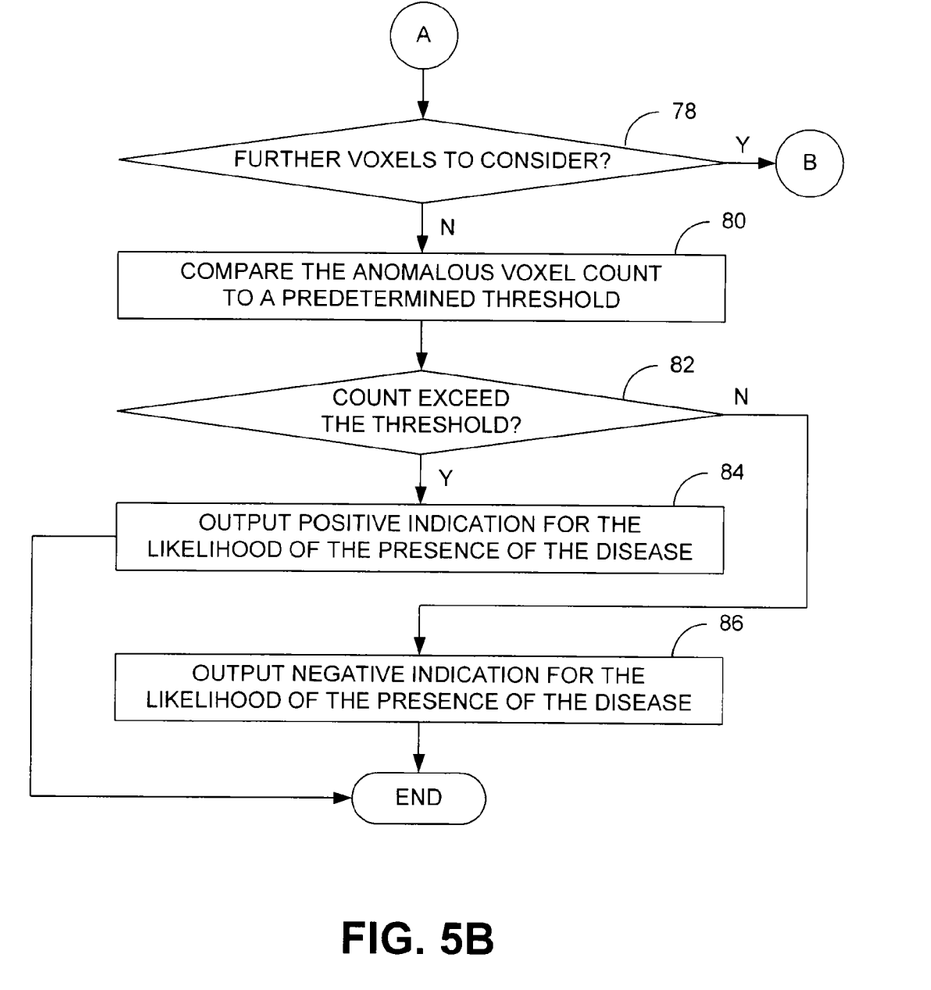

FIGS. 5A and 5B describe a further method for detecting anomalous material in tissue. Beginning with block 60, each of T1, T2, and T2* relaxometry scans are performed on a patient so that, as indicated in block 62, the T1, T2, and T2* relaxometry data is recorded. Referring next to block 64, a voxel of the relaxometry data is identified. At this point, multiple parameters of the voxel can then be identified, as indicated in block 66. Multiple example parameters are described below.

One parameter that can be considered is the speed of decay of the T1, T2, or T2* relaxometry signal. These parameters are time constants of monoexponential decay, which define the speed of signal decay at each point in time. The parameters can be referred to as the T1 monoexponential time constant, the T2 monoexponential time constant, and the T2* monoexponential time constant, respectively. The parameters can be defined mathematically as:

$$m_1 = \ln[I(t)/I_0]/t \quad \text{[Equation 1]}$$

where $m_1$ is the monoexponential time constant, I is the intensity of the relaxometry signal, $I_0$ is the intensity at some initial time, and t is time. Generally speaking, the faster the speed of decay of the relaxometry signal, the more likely that the tissue represented by the voxel contains an anomalous material, such as iron.

With each of the foregoing parameters, a monoexponential time constant is considered. It is noted, however, that the recorded decay curves may be biexponential. Specifically, it is possible that the decay of a B-one vector near an anomalous material, such as iron, might be distorted enough to generate a second superimposed decay time constant, which would mean that the decay curve is the result of two superimposed rates of decay having different time constants. In view of this, three other parameters that can be considered are the T1, T2, and T2* biexponential time constants.

Other parameters that can be considered are the differences between the T1, T2, and T2* monoexponential and biexponential time constants and the corresponding time constants of neighboring voxels. In particular, a cross-correlation CC(p,q) between the voxel under consideration p and a neighboring voxel q can be determined using the following relation:

$$CC(p, q) = \frac{(I_p - \bar{I}_p) \cdot (I_q - \bar{I}_q)}{|I_p - \bar{I}_p||I_q - \bar{I}_q|},$$ [Equation 2]

where $$I_p(I_p(t_i) \ldots, I_p(t_n)), \bar{I}_p = \frac{1}{n}\sum_{i=1}^{n} I_p(t_i)$$

and $I_p(t_i)$) is the intensity at voxel p measured at time $t=t_i$ (i=1, Idots, n). $I_q$ is similarly defined. The difference between the voxels can then be defined as $$m_2 = \sum_{q \in O_p} CC(p, q)/|O_p|$$ [Equation 3]

where $|O_p|$ denotes the total number of neighboring voxels of p. In this manner, the time constants of the voxel under consideration can be compared to the average of the corresponding time constants of neighboring voxels. What is considered to be a "neighboring" voxel can be, for example, each voxel that is immediately adjacent (i.e., physically proximate) the voxel under consideration in three dimensions. In other embodiments, the neighboring voxels can also include voxels beyond the immediately adjacent voxels. In such a case, the voxels that should be included as neighbors can determined through optimization. In still other embodiments, the neighboring voxels can be defined over the frequency domain, in which case the neighboring voxels may not be limited to those that are physically proximate. In general, when the time constant of the voxel under consideration decays more quickly than those of its neighboring voxels, it is more likely that the tissue associated with the voxel under consideration contains anomalous material.

While comparison of like time constants (e.g., comparison of the T1 time constant of the voxel under consideration with the T1 time constants of the neighboring voxels) has been described above, it is noted that, in some embodiments, it may be beneficial to compare different time constants. For example, it may be beneficial to compare a T1 time constant of the voxel under consideration with the T2 time constant or the T2* time constant of its neighbors. As a further example, it may be beneficial to compare the correlation to its neighbors of a T2 time constant of the voxel under consideration with the similar correlation of the T1 time constant or T2* time constant of its neighbors.

Other parameters that can be considered are those that describe how closely the T1, T2, and T2* monoexponential or biexponential relaxometry signals fit a monoexponential function. As noted above, when tissue contains anomalous material, such as iron, the relaxometry signal may be the result of multiexponential decay. Therefore, the better the relaxometry signal can be fit to a monoexponential curve, the less likely the tissue associated with the voxel contains anomalous material. The fit of the relaxometry signal can be determined by calculating a least squares error between the signal and the monoexponential curve. This can be achieved by first minimizing the following objective function to get the optimal monoexponential fitting curve $$(\hat{A}, \hat{B}, \hat{C}) = argmin_{A,B,C}\sum_{i}|I(t_i) - (A + B\exp\{-Ct_i\})|$$ [Equation 4]

where (A+Bexp $\{-Ct_i\}$) is a monoexponential function and A, B, and C are variables that are selected to minimize the distance between the decay curve and the exponential function.

Once the various parameters have been identified, each parameter can be multiplied by a weighting factor or coefficient to obtain multiple weighted parameters, as indicated in block 68. As described above, the weighting coefficients may be different for each parameter and can be determined through clinical testing relative to the particular disease that is being diagnosed. In particular, weighting can be determined by applying logistic regression on training data sets obtained from the clinical testing.

Referring next to block 70, the weighted parameters can then be summed to obtain a score for the voxel. This score $S_P$ can be mathematically described as $$S_p = \sum_{i=0}^{4} \beta_i m_i$$ [Equation 5]

where $\beta_i$ are the weighting coefficients and $m_i$ are the parameters. In some embodiments, the weighting coefficients are optimized from a learning process of the existing data. The determination of $\beta_i$ requires sufficient data, a good learning model and an efficient optimization algorithm.

The score that is obtained is indicative of the likelihood of the tissue associated with the voxel under consideration contains an anomalous material, such as iron. In some embodiments, the higher the score, the higher the likelihood that the tissue contains the anomalous material. A threshold can be developed, again based upon clinical data, that can be used to evaluate the score. For example, if the score exceeds the threshold, it can be assumed that the tissue contains the anomalous material. On the other hand, if the score is equal to or below the threshold, it can be assumed that the tissue does not contain clinically significant anomalous material. With continued reference to FIG. 5A, if the score exceeds the threshold (block 74), flow continues to block 76 and an anomalous voxel count is iterated. If the score does not exceed the threshold, however, the count is not iterated. In some embodiments, the scores can be weighted by their significance. For example, voxels having a score that is significantly beyond the threshold could be weighted to contribute more to the total score than those having scores just beyond the threshold. Such weighting can also be optimized based on separation of clinically relevant groups in trials.

Regardless of whether or not the count is iterated, flow continues onto block 78 of FIG. 5B and it can be determined whether or not there are further voxels to consider. If so, flow returns to block 64 of FIG. 5A and the process described above can be repeated. If not, however, flow continues to block 80 at which the anomalous voxel count is compared to a further threshold. With reference to decision block 82, if the count exceeds the threshold, it can be assumed that the patient has the disease (e.g., Alzheimer's disease) that is being diagnosed. In such a case, flow continues to block 84 and a positive indication of the likelihood of the presence of the disease can be output to the physician. If the count does not exceed the threshold, however, it can be assumed that the patient does not have the disease and a negative indication of the likelihood of the presence of the disease can be output to the physician, as indicated in block 86.

Although the above-described systems and methods have been discussed in the context of diagnosing Alzheimer's disease, it is emphasized that they could be extended to other pathological iron deposits that occur in association with stroke, coronary artery disease, and cancer, as well as other neurodegenerative disorders such as Parkinson's disease. It is further emphasized that although the above-described systems and methods have been discussed in detail in the context of detecting iron in tissue, the systems and methods could be used to detect the presence of other anomalous materials within such tissue.

The invention claimed is:

1. A method for detecting the presence of anomalous material within tissue, the method comprising:
    scanning a patient using magnetic resonance imaging (MRI) to obtain MRI data, wherein the scanning the patient comprises two or more of performing a T1 relaxometry scan, performing a T2 relaxometry scan, and performing a T2* relaxometry scan;
    identifying individual voxels of the MRI data;
    identifying multiple parameters of each voxel, wherein the multiple parameters comprise two or more of a T1 time constant of the voxel, a T2 time constant of the voxel, a T2* time constant of the voxel, how closely a T1 relaxometry signal of the voxel fits a monoexponential function, how closely a T2 relaxometry signal of the voxel fits a monoexponential function, how closely a T2* relaxometry signal of the voxel fits a monoexponential function, and a cross correlation of a relaxometry signal of the voxel and relaxometry signals of neighboring voxels; and
    assigning a score to each voxel, wherein the score is a summation of the parameters after being multiplied by weighting coefficients that take into account the parameters' significance in a prediction of the presence of the anomalous material; and
    determining as to each voxel based upon the score a likelihood of tissue represented by the voxel containing anomalous material.

2. The method of claim 1, wherein scanning the patient comprises performing the T1 relaxometry scan.

3. The method of claim 1, wherein scanning the patient comprises performing the T2 relaxometry scan.

4. The method of claim 1, wherein scanning the patient comprises performing the T2* relaxometry scan.

5. The method of claim 1, wherein identifying multiple parameters comprises identifying the T1 time constant, the T2 time constant, and the T2* time constant of the voxel.

6. The method of claim 5, wherein the time constants are monoexponential time constants.

7. The method of claim 5, wherein the time constants are biexponential time constants.

8. The method of claim 1, wherein identifying multiple parameters further comprises identifying one or more of a difference between the T1 time constant of the voxel and an average of the T1 time constants of neighboring voxels, a difference between the T2 time constant of the voxel and an average of the T2 time constants of neighboring voxels, and a difference between the T2* time constant of the voxel and an average of the T2* time constants of neighboring voxels.

9. The method of claim 8, wherein the time constants are monoexponential time constants.

10. The method of claim 8, wherein the time constants are biexponential time constants.

11. The method of claim 8, wherein neighboring voxels are voxels that are immediately adjacent a voxel under consideration.

12. The method of claim 1, wherein identifying multiple parameters further comprises identifying one or more of how closely the T1 relaxometry signal of the voxel fits the monoexponential function, how closely the T2 relaxometry signal of the voxel fits the monoexponential function, and how closely the T2* relaxometry signal of the voxel fits the monoexponential function.

13. The method of claim 12, wherein the relaxometry signals are monoexponential.

14. The method of claim 12, wherein the relaxometry signals are biexponential.

15. The method of claim 1, wherein determining the likelihood that the tissue contains anomalous material comprises determining the likelihood that the tissue contains iron.

16. The method of claim 1, further comprising, for each voxel, comparing the score to a threshold and, if the score exceeds the threshold, incrementing an anomalous voxel count.

17. The method of claim 16, further comprising comparing the anomalous voxel count to a further threshold and, if the count exceeds the further threshold, outputting a positive indication for the likelihood of the presence of a disease.

18. The method of claim 17, wherein the disease is Alzheimer's disease.

19. The method of claim 1, wherein the identifying multiple parameters comprises identifying the T1 time constant of the voxel, the T2 time constant of the voxel, the T2* time constant of the voxel, the cross-correlation of the relaxometry signal of the voxel and relaxometry signals of neighboring voxels, and how closely the T2 time constant of the voxel fits the monoexponential function.

20. A non-transitory computer-readable medium comprising logic configured to, when executed by a processor, causes the processor to:
    identify individual voxels of magnetic resonance imaging (MRI) data obtained from a patient, wherein the MRI data comprises two or more of T1 relaxometry data, T2 relaxometry data, and T2* relaxometry data;
    identify multiple parameters of each voxel, wherein the multiple parameters comprise two or more of a T1 time constant of the voxel, a T2 time constant of the voxel, a T2* time constant of the voxel, how closely a T1 relaxometry signal of the voxel fits a monoexponential function, how closely a T2 relaxometry signal of the voxel fits a monoexponential function, how closely a T2* relaxometry signal of the voxel fits a monoexponential function, and a cross correlation of a relaxometry signal of the voxel and relaxometry signals of neighboring voxels;
    assign a score to each voxel, wherein the score is a summation of the parameters after being multiplied by weighting coefficients that take into account the parameters' significance in a prediction of a presence of an anomalous material; and
    determine as to each voxel based upon the score a likelihood of tissue represented by the voxel containing anomalous material.

21. The non-transitory computer-readable medium of claim 20, wherein the logic configured to identify multiple parameters comprises logic configured to identify the T1 time constant, the T2 time constant, and the T2* time constant of the voxel.

22. The non-transitory computer-readable medium of claim 20, wherein the logic configured to identify multiple parameters further comprises logic configured to identify one or more of a difference between the T1 time constant of the voxel and an average of the T1 time constants of neighboring voxels, the T2 time constant of the voxel and an average of the T2 time constants of neighboring voxels, and the T2* time constant of the voxel and an average of the T2* time constants of neighboring voxels.

23. The non-transitory computer-readable medium of claim 20, wherein the logic configured to identify multiple parameters further comprises logic configured to identify one or more of how closely the T1 relaxometry signal of the voxel fits the monoexponential function, how closely the T2 relaxometry signal of the voxel fits the monoexponential function, and how closely the T2* relaxometry signal of the voxel fits the monoexponential function.

24. The non-transitory computer-readable medium of claim 20, wherein the logic configured to determine the likelihood that the tissue contains anomalous material comprises logic configured to determine the likelihood that the tissue contains iron.

25. The non-transitory computer-readable medium of claim 20, further comprising logic configured to compare the score of each voxel to a threshold and, if the score exceeds the threshold, increment an anomalous voxel count.

26. The non-transitory computer-readable medium of claim 25, further comprising logic configured to compare the anomalous voxel count to a further threshold and, if the count exceeds the further threshold, output a positive indication for the likelihood of the presence of a disease.

27. The non-transitory computer-readable medium of claim 20, wherein the logic configured to identify multiple parameters comprises logic configured to identify the T1 time constant of the voxel, the T2 time constant of the voxel, the T2* time constant of the voxel, the cross-correlation of the relaxometry signal of the voxel and relaxometry signals of neighboring voxels, and how closely the T2 time constant of the voxel fits the monoexponential function.

* * * * *